United States Patent [19]
Deghenghi

[11] Patent Number: 6,077,523
[45] Date of Patent: Jun. 20, 2000

[54] PROCESS TO MANUFACTURE IMPLANTS CONTAINING BIOACTIVE PEPTIDES

[76] Inventor: Romano Deghenghi, Cheseaux Dessus B1, St. Cergue, Switzerland

[21] Appl. No.: 09/311,744

[22] Filed: May 14, 1999

Related U.S. Application Data

[62] Division of application No. 08/897,942, Jul. 21, 1997, Pat. No. 5,945,128.
[60] Provisional application No. 60/025,444, Sep. 4, 1996.

[51] Int. Cl.$^7$ .............................. A61F 2/02; A61K 9/50; B01J 13/02
[52] U.S. Cl. ......................... 424/426; 424/501; 424/502; 264/4.1
[58] Field of Search ..................................... 424/422, 426, 424/501, 502; 264/4.1

[56] References Cited

U.S. PATENT DOCUMENTS

| | | | |
|---|---|---|---|
| 5,134,122 | 7/1992 | Orsolini | 514/15 |
| 5,192,741 | 3/1993 | Orsolini et al. | 514/4 |
| 5,225,205 | 7/1993 | Orsolini | 424/489 |
| 5,439,688 | 8/1995 | Orsolini et al. | 424/489 |
| 5,456,917 | 10/1995 | Wise et al. | 424/426 |

FOREIGN PATENT DOCUMENTS

| | | |
|---|---|---|
| 2 234 169 | 1/1991 | United Kingdom . |
| 2 249 725 | 5/1992 | United Kingdom . |

*Primary Examiner*—Carlos A. Azpuru
*Attorney, Agent, or Firm*—Pennie & Edmonds LLP

[57] ABSTRACT

A pharmaceutical implant for the delivery of an effective amount of a bioactive peptide or peptide analog over a period of 1 to 12 months. This implant has a diameter of about 1 to 2 mm, a length of between about 10 and 25 mm and is obtainable from a process which includes the steps of grinding a copolymer of lactic acid and glycolic acid having a ratio of glycolide to lactide units of from about 0 to 5:1 to a particle size of between about 50 and 150 μm; sterilizing the ground copolymer with a dose of between about 1 and 2.5 Mrads of ionizing γ-radiation; wetting the ground and sterilized copolymer with a sterile aqueous slurry of a bioactive peptide or peptide analog; aseptically blending the copolymer and the slurry to obtain a homogeneous mixture of the copolymer and between about 10 and 50% of the bioactive peptide or peptide analog; drying the mixture at reduced pressure and at temperature not exceeding 25° C.; aseptically extruding the dried mixture at a temperature between about 70 and 110° C.; and aseptically cutting a cylindrical rod from the extruded mixture to form the pharmaceutical implant.

15 Claims, 3 Drawing Sheets

PROCESS TO MANUFACTURE IMPLANTS CONTAINING BIOACTIVE PEPTIDES

This application is a divisional of U.S. application Ser. No. 08/897,942 filed Jul. 21, 1997, now U.S. Pat. No. 5,945,128, which is a continuation of provisional application Ser. No. 60/025,444 filed Sep. 4, 1996.

TECHNICAL FIELD

The invention relates to a novel process for preparing implants of bioactive peptides or peptide analogs where such implants have a more uniform distribution of peptide or peptide analog therein.

BACKGROUND ART

A wide variety of bioactive peptides and peptide analogs have been used as active agents for the treatment of various conditions. These active agents are generally administered in connection with a polymeric delivery system to control the release of the agent. For example, peptide analogs of the natural hypothalamic hormone LHRH (Luteinizing Hormone Releasing Hormone, a decapeptide) are of therapeutic value when administered for a prolonged period of time with the appropriate delivery system. Commercially successful delivery systems include microspheres, microcapsules, microgranules and other implant forms which, when injected subcutaneously or intramuscularly, release the LHRH analog from a biocompatible and biodegradable matrix. The matrix is frequently a copolymer of lactic and glycolic acid ("PLGA", polylactic glycolic acid) as described, for example, in U.S. Pat. Nos. 3,773,919, 3,887,499, 4,675,189, 4,767,628 and many others.

It has been assumed that a continuous or monophasic release of such bioactive agents is a highly desirable feature of such formulations (see, e.g., U.S. Pat. No. 5,366,734). In fact, it has now been realized that what is really needed is to have the "therapeutic" effect of the peptide or peptide analog be maintained or sustained over a relatively long span of time (e.g., three to six months or longer). Thus, improvements in this area are desired and necessary.

SUMMARY OF THE INVENTION

The present invention relates to a process for manufacturing pharmaceutical implants for the delivery of an effective amount of a bioactive peptide or peptide analog over a period of 1 to 12 months which comprises: grinding a copolymer of lactic acid and glycolic acid having a ratio of glycolide to lactide units of from about 0 to 5:1 to a particle size of between about 50 and 150 µm; wetting the ground copolymer with an aqueous slurry of a bioactive peptide or peptide analog; blending the copolymer and the slurry to obtain a homogeneous mixture of the copolymer and between about 10 and 50% of the bioactive peptide; drying the mixture at reduced pressure and at a temperature not exceeding 25° C.; extruding the dried mixture at a temperature between about 70 and 110° C.; and cutting cylindrical rods of about 1 to 2 mm diameter and between about 10 and 25 mm in length from the extruded mixture to form the implants.

Advantageously, the ground copolymer is sterilized with a dose of between about 1 and 2.5 Mrads of ionizing γ-radiation before being combined with the bioactive peptide, and the blending, extruding and cutting steps are conducted under aseptic conditions. Also, the implants are generally sterilized in a conventional manner prior to being administered to the subject or patient.

The polymers or copolymers form a biodegradable matrix within which is contained a uniform distribution of the peptide or peptide analog. In these copolymers, an advantageous ratio of glycolide to lactide units ranges from about 0.5:1 to 3:1. One particularly preferred copolymer to be used is soluble in benzene and has an inherent viscosity of from 0.51 to 1 (1% in benzene). The amount of slurry is preferably controlled so that the amount of water in the mixture is between about 35 and 65 ml. per 100 grams copolymer, so that the amount of bioactive peptide in these rods is between about 10 to 50 percent by weight.

The bioactive peptide or peptide analog may be an agonist or antagonist of LHRH, GnRH, growth hormone releasing hormone, growth hormone releasing peptide, angiotensin, bombesin, bradykin, cholecystokinin, enkephalin, neurokinin, tachykinin or substance P. The bioactive peptide may also be an inhibitor such as a renin inhibitor, a protease inhibitor, a metallopeptidase inhibitor, enkephalinase and atrial or brain natriuretic factor degrading enzyme inhibitor. The LHRH analog is preferably a pharmaceutically acceptable salt of an LHRH agonist or antagonist, such as a pharmaceutically acceptable salt of leuprolide, goserelin, triptorelin, buserelin, avorelin, deslorelin, histrelin, cetrorelix, teverelix, ramorelix, antide, nictide, azaline B, azaline C or ganirelix.

Another aspect of the invention relates to the pharmaceutical implants obtained according to the process defined herein. These implants are preferably contained in an implanter device with a retractable needle so that they are suitable for subcutaneous injection under the skin of a mammal.

DETAILED DESCRIPTION OF THE PREFERRED EMBODIMENTS

Figure 1:
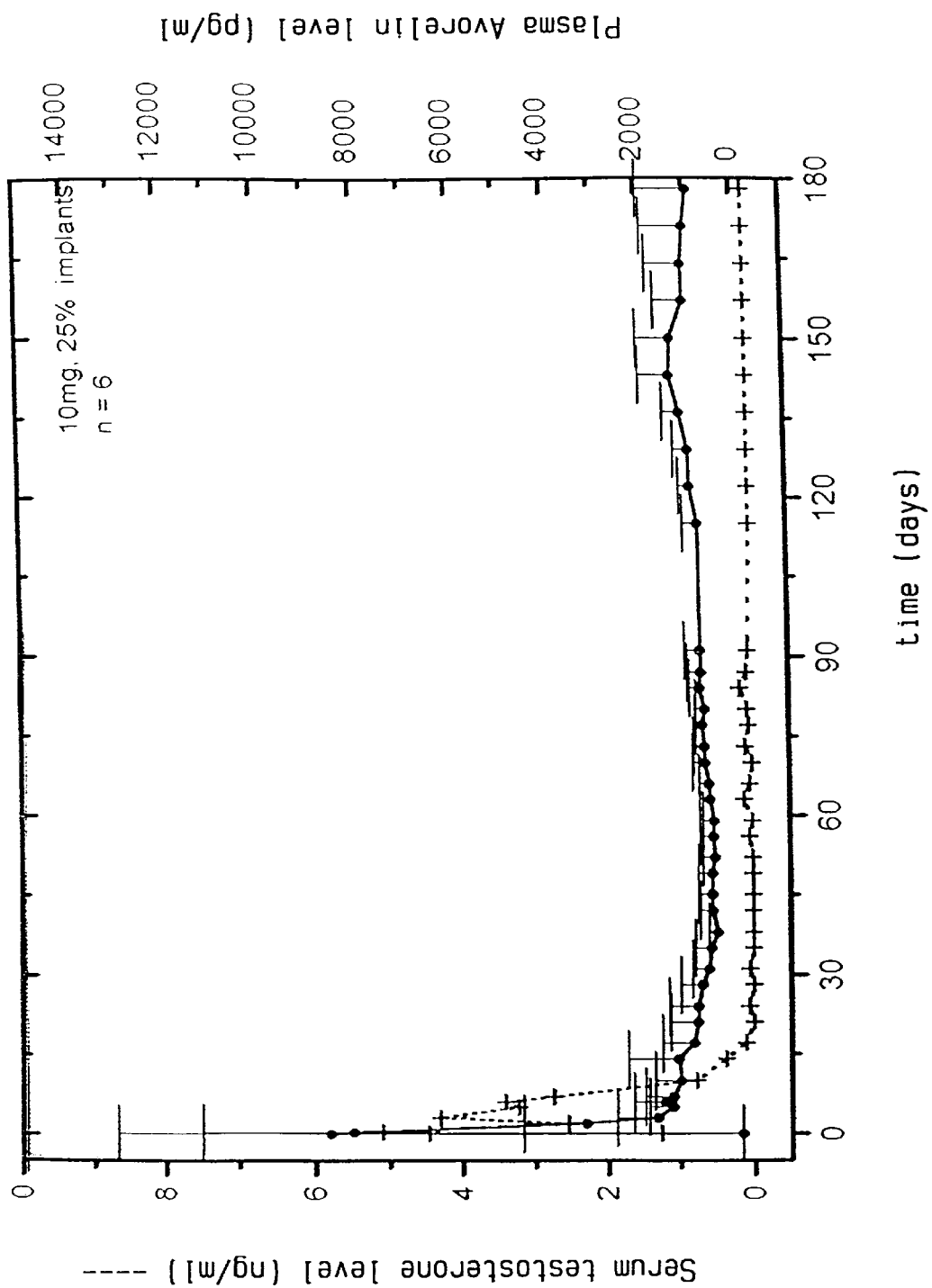
FIG. 1 is a graph of serum testosterone and plasma avorelin levels of male beagle dogs for up to 180 days after injection of the avorelin implants of Example 1 of the invention.

Any polylactide polymer or PLGA copolymer can be used to form the biodegradable matrix of this invention. These materials are well known to one of ordinary skill in the art, e.g., in the U.S. patents mentioned above, and need not be further discussed herein. The particular copolymer is selected and then is ground to a particle size of between about 50 and 150 µm. This grinding step is also conventional and needs no further explanation.

In the most preferred method, the ground copolymer is sterilized with a dose of between about 1 and 2.5 Mrads of ionizing γ-radiation, again in a conventional manner that is well known to one of ordinary skill in the art.

The ground and sterilized copolymer particles are then wetted with a sterile aqueous slurry of an active agent of a bioactive peptide or peptide analog. This slurry is made by combining the peptide, analog, or a pharmaceutically acceptable salt thereof in sterile water. The amount of the active agent can vary over a wide range, from e.g. about 5 to 50 and preferably about 10 to 25 grams per liter. The solution is then sterilized in a conventional manner, such as by passage through a sterilizing filter. If necessary, the solution can be concentrated to increase the amount of peptide or peptide analog therein. The concentration of the peptide or peptide analog in the solution can be varied to change the resulting dosage of the implant.

Next, the copolymer and the slurry are aseptically blended to obtain a homogeneous mixture of the copolymer and the active agent. Depending upon the desired formulation, the active agent represents between about 10 and 50% and preferably about 15 to 25% of the mixture. As noted above, a water content of about 35 and 65 ml. and preferably about 45 to 55 ml. per 100 grams copolymer in the mixture is desired. Next, the mixture is dried at reduced pressure and at a temperature not exceeding 25° C. to form the pharmaceutical composition. If necessary, this composition can be formulated with conventional carriers as a suspension for injection.

Alternatively, the dried composition can be extruded with a conventional extrusion device at a temperature between about 70 and 110° C. to form a "spaghetti" or continuous rod product. The use of heat in the extrusion step helps further dry the product. To form the implants, these cylindrical rods are aseptically cut into pieces of about 1 to 2 mm diameter and between about 10 and 25 mm in length from the extruded mixture. The length of the implant is another mechanism for varying the dosage of bioactive peptide of peptide analog therein. These products can then be implanted subcutaneously beneath the skin of the patient using conventional implanting devices.

The present invention provides an effective release (i.e. in terms of therapeutic effectiveness) of a bioactive peptide, or peptide analog, such as an LHRH analog, even if such release, as measured by plasma level of the peptide, or peptide analog, is intermittent or discontinuous. This effectiveness can be achieved, for example, by the internalization or down-regulation of pituitary receptors following their exposure to LHRH agonists or to LHRH antagonists which are intrinsically long acting.

The process of this invention can be applied to a wide variety of peptides or peptide analogs. In addition to LHRH analogs herein mentioned, GnRH or growth hormone releasing hormones or peptides can be mentioned. Generally, any peptides or peptide analogs that are chemically stable under the process conditions and that provide a sustained delivery is desirable from a therapeutic point of view. Non-limiting examples of such peptides and peptide analogs are somatostatin and somatostatin analogs, agonist and antagonist analogs of angiotensin II, bombesin analogs, preferably bombesin antagonists, bradykinin antagonists, preferably with minimal histamine releasing properties, cholecystokinin analogs, preferably cholecystokinin antagonists, enkephalin analogs, neurokinins, tachykinins and substance P antagonists, renin inhibitors and other aspartyl protease inhibitors, such as HIV protease inhibitors, metallopeptidase inhibitors, such as angiotensin converting enzyme, enkephalinase and atrial or brain natriuretic factor degrading enzyme inhibitors. The skilled artisan will favor those peptides and peptidomimetic compounds which are not, or are poorly, absorbed by the oral route in animals and humans, and will adjust the dose of the compound to be formulated in the implants of the present invention according to the biological potency of such compound, the necessary daily effective dose and the estimated duration of release from the formulation.

The present invention also eliminates contamination of such formulations with organic solvents, particularly chlorinated ones, such as chloroform or methylene chloride, which are typically utilized in the manufacture of microspheres or microcapsules by the coacervation-solvent evaporation methods (see, e.g., U.S. Pat. No. 3,773,919) or which are used to sterilize PLGA copolymers by filtration.

The present invention does not make use of any organic solvent, but takes advantage of the unorthodox use of water, a solvent hitherto considered unsuitable for such formulations because of its deleterious effect on the polyester (copolymer) of the PLGA matrix, where it can accelerate chemical hydrolysis and also damage structural integrity upon exposure to ionizing radiation (formation of free radicals) during the sterilization step necessary for safety considerations.

Another advantage of this unorthodox use of water is to achieve a uniform coating of the active principle on the granulated polymer powder, resulting in a much needed and highly desired uniformity of the mixture, an essential condition of the manufacturing process. A further unexpected advantage of this unconventional solvent is the "wettability" of the powdery mixture which would otherwise create serious problems due to formation of static electrical charges which can cause unacceptable mechanical losses and loss of uniformity.

The instant process further provides with a simple method of sterilization of the composition by subjecting the polymer to ionizing radiation prior to blending the polymer with the bioactive peptides or peptide analogs which are invariably damaged by such radiation, resulting in unwanted byproducts. A further advantage of the instant process is to provide a variable sterilizing dose of radiation (from 1 to 2.5 Mrad) predetermined by the actual biomass present in the co-polymer, with a resulting safety without undue creation of radiolysis artifacts.

EXAMPLES

The following examples are submitted to illustrate the effectiveness of the most preferred formulations of the invention.

Example 1

The manufacturing process is conducted in a commercially available isolator (ARFL, Neuilly-sur-Marne, France) equipped with air-locks for the introduction of pre-sterilized components and itself sterilized by previous peracetic acid treatment. The extrusion machine is a commercially available single screw extruder (Brabender, 47055 Duisburg, Germany) equipped with pressure and temperature probes. The cutting machine is commercially available (Davis-Standard Corp. Cedar Grove, N.J., USA). Blenders/mixers and weighing instruments are conventional equipment.

A quantity of 80 g of racemic lactic acid and glycolic acid copolymer (75:25) soluble in benzene and of inherent viscosity of 0.60 (1% in benzene) (PuracBiochem B.V., Gorinchem, Netherlands) is ground and sieved to collect the fraction of particles between 50 to 150 μm and sterilized with an ionizing γ-radiation of 1.5 Mrads by a commercial laboratory (Caric-Mediris, Fleurus, Belgium) and introduced through the air-lock into the sterile isolator.

Separately, 23 grams of the LHRH analog avorelin acetate (INN), or (2Methyl-D-Trp)$^6$(des-Gly)$^{10}$(ProEthylamide)$^9$LHRH acetate, dissolved in 500 ml of sterile water and filtered through a Millipore 0.2 μm sterilizing filter. The sterile solution is reduced by evaporation to a volume of 50 ml and the resulting mixture is dispersed through the ground co-polymer. The wet mixture is blended to obtain a granulate containing 20% of avorelin. Such mixture is dried at 25° C. under reduced pressure and then extruded at a temperature gradient from 70 to 110° C. at pressures of 3500 p.s.i. The resulting extrudate is aseptically cut to give rods of 1.5 mm diameter and 15 mm long, containing 10 mg avorelin, which are inserted into a pre-sterilized implanter with a retractable needle (SFM GmbH, D-6480 Wächtersbach, Germany) sealed and used as such, or optionally further sterilized with a dose of 1.5 Mrad of γ-radiation before clinical use.

When implanted s.c. into male beagle dogs, after the initial stimulation of LH and testosterone, castration levels of testosterone were maintained for 6 months. The plasma levels of avorelin, after a short-lived burst, fell to a nadir at 40 days and rose again at 120 days before becoming undetectable at day 160. These results are shown in FIG. 1.

Example 2

Figure 2:
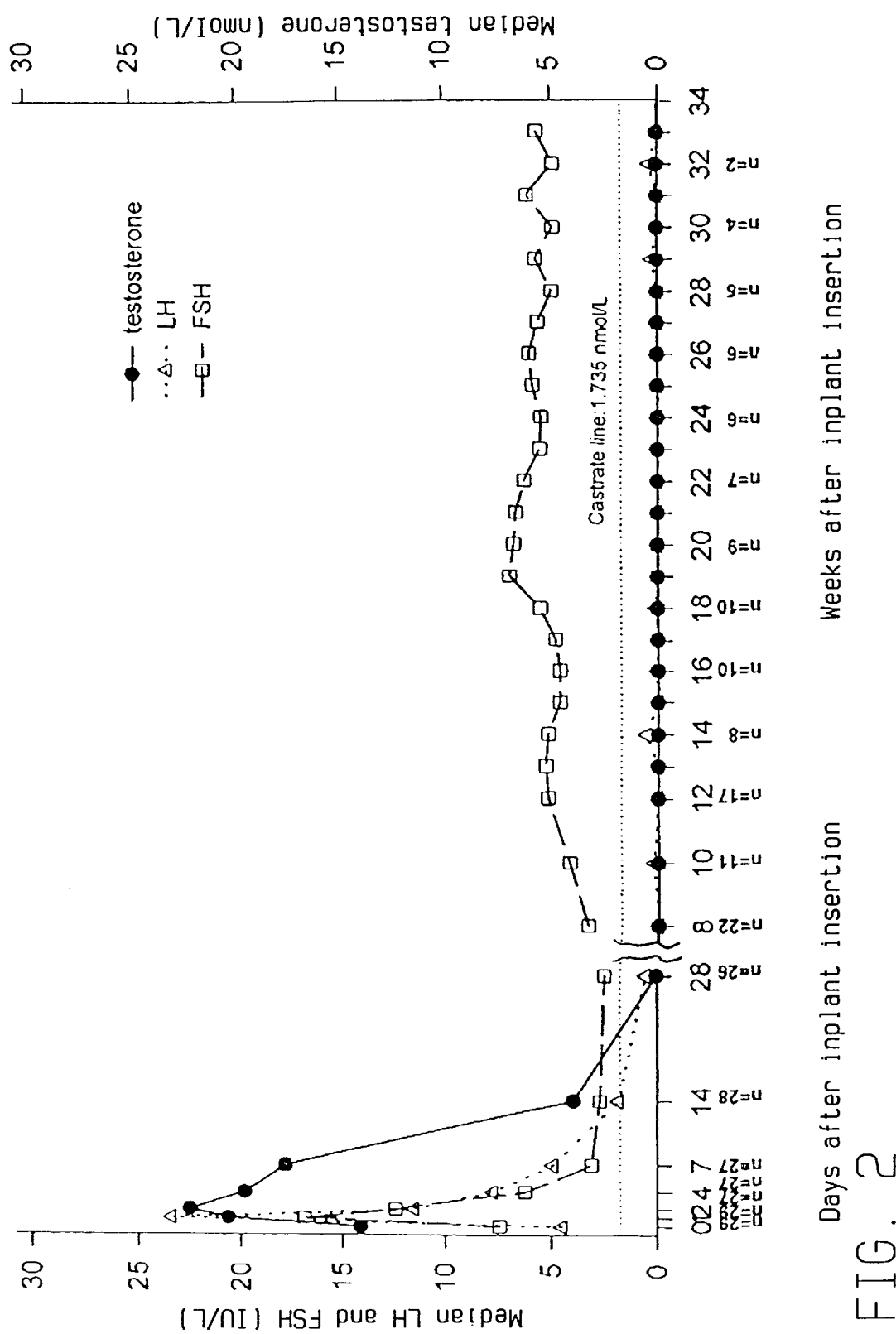
FIGS. 2 and 3 are graphs of serum LH, FSH and testosterone levels in male patients for up to 33 to 35 weeks after injection of the avorelin implants of Examples 2 and 3 of the invention.

Following essentially the procedure of Example 1, 10 mg avorelin implants were prepared, further sterilized, and implanted into healthy male patients. After initial stimulation of LH, FSH and testosterone, these levers were significantly reduced, with the testosterone level being maintained below a castration level for 33 weeks. These results are shown in FIG. 2.

Example 3

Figure 3:
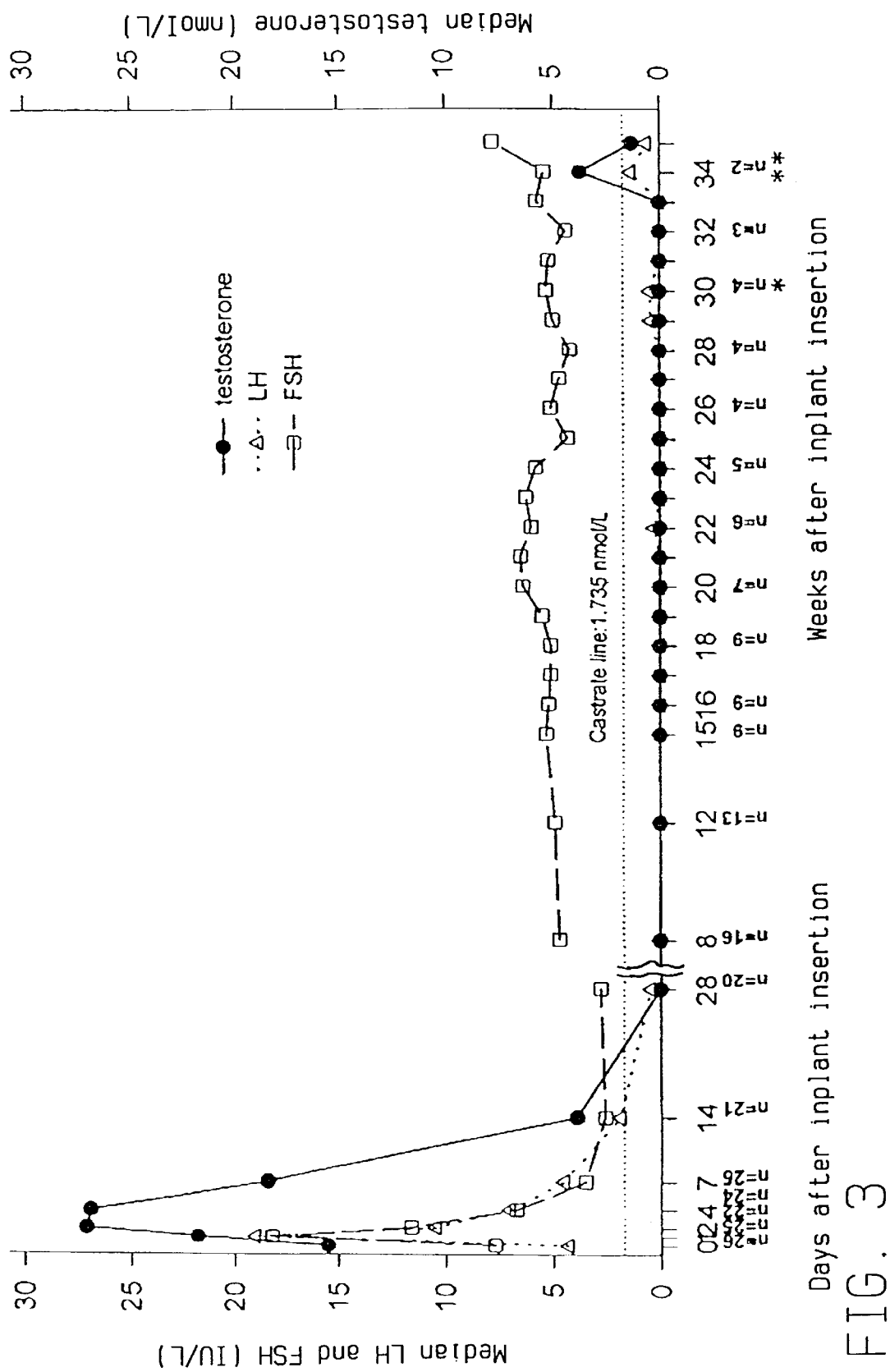

Following essentially the procedure of Example 2, except that the length of the implant was increased to provide a dose of avorelin of 15 mg was prepared. These implants were sterilized and implanted into healthy male patients. After initial stimulation of LH, FSH and testosterone, these levels were significantly reduced, with the testosterone level being maintained below a castration level for 33 weeks. These results are shown in FIG. 3.

Example 4

Following essentially the procedure of Example 1 with appropriate modifications required by the individual LHRH analog, rods containing 22 mg of leuprolide, 10 mg of goserelin and 30 mg of teverelix were similarly obtained.

what is claimed is:

1. A pharmaceutical implant for the delivery of an effective amount of a bioactive and water-soluble peptide or peptide analog over a period of 1 to 12 months, said implant having a diameter of about 1 to 2 mm and a length of between about 10 and 25 mm and being obtainable from a process which comprises:

grinding a copolymer of lactic acid and glycolic acid having a ratio of glycolide to lactide units of from about 0 to 5:1 to a particle size of between about 50 and 150 μm;

wetting said ground and sterilized copolymer with a sterile aqueous slurry of a bioactive peptide or peptide analog;

blending the copolymer and the slurry to obtain a homogeneous mixture of said copolymer and between about 10 and 50% of the bioactive peptide or peptide analog;

drying said mixture at reduced pressure and at temperature not exceeding 25° C.;

extruding said dried mixture at a temperature between about 70 and 110° C.; and cutting a cylindrical rod from the extruded mixture to form the pharmaceutical implant.

2. The implant of claim 1 wherein the process further comprises sterilizing said ground copolymer with a dose of between about 1 and 2.5 Mrads of ionizing γ-radiation before adding the aqueous slurry thereto.

3. The implant of claim 1 wherein the process further comprises conducting the blending, extruding and cutting steps are conducted aseptically.

4. The implant of claim 1 wherein the process further comprises selecting the copolymer to be used to be one which is soluble in benzene and has an inherent viscosity of from 0.51 to 1 (1% in benzene).

5. The implant of claim 1 wherein the amount of slurry is controlled so that the amount of water in the mixture is between about 35 and 65 ml. per 100 grams copolymer.

6. The implant of claim 1 wherein the amount of slurry is controlled so that the amount of bioactive peptide or peptide analog in the rods is between about 10 to 50 percent by weight.

7. The implant of claim 1 wherein the ratio of glycolide to lactide units in the copolymer ranges from about 0.5:1 to 3:1.

8. The implant of claim 1 wherein the bioactive peptide or peptide analog is an agonist or antagonist of LHRH, GnRH, growth hormone releasing hormone, growth hormone releasing peptide, angiotensin, bombesin, bradykin, cholecystokinin, enkephalin, neurokinin, tachykinin or substance P.

9. The implant of claim 1 wherein the bioactive peptide or peptide analog is a renin inhibitor, a protease inhibitor, a metallopeptidase inhibitor, enkephalinase and atrial or brain natriuretic factor degrading enzyme inhibitor.

10. The implant of claim 1 wherein the bioactive peptide or peptide analog is a pharmaceutically acceptable salt of leuprolide, goserelin, triptorelin, buserelin, avorelin, deslorelin, histrelin, cetrorelix, teverelix, ramorelix, antide, nictide, azaline B, azaline C or ganirelix.

11. The implant of claim 1 contained in an implanter device with a retractable needle and suitable for subcutaneous injection under the skin of a mammal.

12. A pharmaceutical implant for the delivery of an effective amount of a bioactive and water-soluble peptide or peptide analog over a period of 1 to 12 months, said implant having a diameter of about 1 to 2 mm and a length of between about 10 and 25 mm and the bioactive peptide or peptide analog is present in the rods in an amount of between about 10 to 50 percent by weight.

13. The implant of claim 12 wherein the bioactive peptide or peptide analog is an agonist or antagonist of LHRH, GnRH, growth hormone releasing hormone, growth hormone releasing peptide, angiotensin, bombesin, bradykin, cholecystokinin, enkephalin, neurokinin, tachykinin or substance P.

14. The implant of claim 12 wherein the bioactive peptide or peptide analog is a renin inhibitor, a protease inhibitor, a metallopeptidase inhibitor, enkephalinase and atrial or brain natriuretic factor degrading enzyme inhibitor.

15. The implant of claim 12 wherein the bioactive peptide or peptide analog is a pharmaceutically acceptable salt of leuprolide, goserelin, triptorelin, buserelin, avorelin, deslorelin, histrelin, cetrorelix, teverelix, ramorelix, antide, nictide, azaline B, azaline C or ganirelix.

* * * * *